(12) United States Patent
Boesveld et al.

(10) Patent No.: US 6,855,857 B2
(45) Date of Patent: Feb. 15, 2005

(54) ISOMERISATION PROCESS

(75) Inventors: Willem Marco Boesveld, Wokingham (GB); Paul Greenough, Beaconsfield (GB)

(73) Assignee: BP Oil International Limited, London (GB)

( * ) Notice: Subject to any disclaimer, the term of this patent is extended or adjusted under 35 U.S.C. 154(b) by 0 days.

(21) Appl. No.: 10/398,765

(22) PCT Filed: Oct. 5, 2001

(86) PCT No.: PCT/GB01/04461
§ 371 (c)(1),
(2), (4) Date: May 29, 2003

(87) PCT Pub. No.: WO02/31089
PCT Pub. Date: Apr. 18, 2002

(65) Prior Publication Data
US 2003/0187316 A1 Oct. 2, 2003

(30) Foreign Application Priority Data
Oct. 11, 2000 (GB) .............................................. 0024888
Jul. 21, 2001 (GB) .............................................. 0117829

(51) Int. Cl.[7] ................................................ C07C 5/27
(52) U.S. Cl. ........................ 585/747; 585/748; 585/749
(58) Field of Search ............................... 585/747, 748, 585/749

(56) References Cited
U.S. PATENT DOCUMENTS

| | | | |
|---|---|---|---|
| 2,583,739 A | 1/1952 | Kemp et al. | |
| 3,766,286 A | 10/1973 | Olah | |
| 3,839,489 A | * 10/1974 | Mahan et al. | ................ 585/747 |
| 3,867,476 A | 2/1975 | Torck | |
| 3,962,133 A | 6/1976 | Rodewald | |
| 4,098,833 A | 7/1978 | Wristers | |
| 4,229,611 A | * 10/1980 | Kramer | ....................... 585/728 |
| 4,246,094 A | 1/1981 | McCaulay et al. | |
| 4,311,868 A | 1/1982 | Ueno et al. | |
| 4,472,268 A | 9/1984 | Olah | |
| 4,613,723 A | 9/1986 | Olah | |

FOREIGN PATENT DOCUMENTS

| | | |
|---|---|---|
| FR | 2 300 749 | 9/1976 |
| FR | 2 771 419 | 5/1999 |
| WO | WO 00/03801 | 1/2000 |

OTHER PUBLICATIONS

Bonifay, R., et al; "Activation des paraffines en milieu superacide $SbF_5$–HF . . . dans le cas du n–pentane et du n–hexane(*)"; M. Bulletin de la Societe Chimique de France; 1977; No. 9–10 pp. 808–814.

Bassir et al; "Cracking of Heptanes in Superacid Antimony Pentafluoride–Hydrofluoric Acid"; Elsevior Science Publ B.V. Amsterdam; 1987.

Kuchar, P.J. et al; "Developments in Isomerisation"; *International Journal of Hydrocarbon Eng.*; 4, pp. 50–57 (1999).

Misonom M. et al; "Solid Superacid Catalysts"; *Chemtech*, pp. 23–29 (1993).

Cheung, T.K. et al; "Strong Solid–Acid Catalysts for Paraffin Conversions"; *Chemtech*, pp. 28–35 (1997).

Rigby, A.M. et al; "Ab initio calculations on the mechanisms of hydrocarbon conversion in zeolites: Skeletal isomerisation and olefin chemisorption"; *J. Mol. Cat. A: Chem.*, 126, pp. 61–72 (1997).

(List continued on next page.)

*Primary Examiner*—Thuan D Dang
(74) *Attorney, Agent, or Firm*—Nixon & Vanderhye

(57) ABSTRACT

A process for the production of triptane, said process comprising: isomerising a hydrocarbon feedstock by containing said feedstock with an isomerisation catalyst at a reaction temperature of −50 to 25° C., and a contact time of 0.01 to 150 hours, such that the triptane selectivety of the isomerisation reaction is at least 5% as a proportion of said hydrocarbon feedstock.

19 Claims, 2 Drawing Sheets

OTHER PUBLICATIONS

Adeeva, V. et al, "Alkane isomerization over sulfated zirconia and other solid acids"; *Topics in Cat.*; 6, pp. 61–76 (1998).

Goeppert, A. et al; "Activation, isomerization and H/D exchange of small alkanes in triflic acid"; *Catalysis Letters*; 56, pp. 43–48 (1998).

Sassi, A. et al; "Isomerization and cracking reactions of branched octanes on sulfated zirconia"; *Applied Catalysis A: General*; 188, pp. 155–162 (1999).

Boronat, M. et al; "Theoretical Study of Bimolecular Reactions between Carbenium Ions and Paraffins: The Proposal of a Common Intermediate for Hydride Transfer, Disproportionation, Dehydrogenation, and Alkylation"; *J. Phys. Chem. B*, 103, pp. 7809–7821 (1999).

Olah, G.A., et al; *Superacids*; (Contents) and pp. 254–266, Wiley, New York, 1985.

Bonnet, B. et al; "Ionic Species in HF–SbF$_5$ Solutions. An Infrared Spectroscopy Investigation"; *Inorg. Chem.*, 19, pp. 785–788; (1980).

Culmann, J.–C. et al; Fluoroanions and cations in the HF–SbF$_5$ superacid system. A $^{19}$F and $^1$H NMR study; *New J. Chem.*, 23, pp. 863–867 (1999).

Olah, G.A. et al; "Stable Carbonium Ions. XLVII.[1] Alkylcarbonium Ion Formation from Alkanes via Hydride (Alkide) Ion Abstraction in Fluorosulfonic Acid–Antimony Pentafluoride–Sulfuryl Chlorofluoride Solution[2]"; *J. Am. Chem. Soc.*, 89, 4739–4744 (1967).

Hogeveen, H. et al; "Chemistry and Spectroscopy in Strongly Acidic Solutions: Electrophilic Substitution at Alkane–carbon by Protons"; *J. Chem. Soc., Chem. Commun.*; pp 635–636 (1967).

*Stable Carbocation Chemistry*; (Contents); Eds. G.K.S. Prakash and P.v.R. Schleyer, Wiley, New York, (1997).

Jost, R. et al; "Deuterium Isotope Effect on the Equilibrium of Methylpentyl Ions. The Ethyl Versus Methyl Shift. A$^1$H NMR Kinetic Study in Superacid Medium"; *Nouveau Journal De Chimie*, vol. 7, No. 2, p. 79 (1983).

Bonifay, R. et al; "Activation des paraffines en milieu superacid SbF$_5$–HF . . . dans le cas du n–pentane et du n–hexane"; *Bull. Soc. Chim. Fr.*, pp. 308–814 (1977).

Bassir, M. et al; "Activite catalytique du superacide SbF$_5$–HF lors de l'isomerisation de l'heptane"; *Bull. Soc. Chim. Fr.*, pp. 760–766, (1987); idem, *New J. Chem.*, 11, p437 (1987).

Patent Abstracts of Japan; JPS 53–133404; Mitsubishi Gas Chem. Co. Inc., (1980).

Sommer, J. et al; "Selective Electrophilic Activation of Alkanes"; *Acc. Chem. Res.*, 26, pp. 370–376 (1993).

* cited by examiner

ISOMERISATION PROCESS

This application is the U.S. national phase of international application PCT/GB01/04461, filed 5 Oct. 2001, which designated the U.S.

The present invention relates to a process for isomerising hydrocarbons. In particular, the present invention relates to a process for selectively isomerising hydrocarbons to obtain triptane (2,2,3-trimethyl butane).

BACKGROUND OF THE INVENTION

Triptane is a highly branched hydrocarbon which can be used as a fuel additive for motor and aviation gasoline because of its high octane rating. It is generally produced by isomerising or reacting aliphatic, cycloaliphatic and/or alkyl aromatic hydrocarbons in the presence of an isomerisation catalyst. An example of such a process is described in U.S. Pat. No. 3,766,286. This document describes the use of reaction temperatures of −30 to 100° C. and contact times of 0.1 to 10 hours. The preferred embodiment, for instance, describes the isomerisation of n-heptane at 25° C. for 5 to 6 hours. The triptane yields obtained were between 0.4 and 1.4 wt %.

SUMMARY OF THE INVENTION

We have now found that by careful selection of reaction temperature and contact time, the selectivity of the isomerisation process towards triptane may be increased.

According to the present invention, there is provided a process for the production of triptane, said process comprising:

isomerising a hydrocarbon feedstock by contacting said feedstock with an isomerisation catalyst at a reaction temperature of −50 to 25° C., and a contact time of 0.01 to 150 hours, such that the triptane selectivity of the isomerisation reaction is at least 5% as a proportion of said hydrocarbon feedstock.

Preferably, the reaction temperature is −30 to 15° C., more preferably, −25 to 10° C., even more preferably, −15 to 5° C., most preferably, −10 to 0° C.

The contact time may be 0.05 to 50 hours, preferably, 0.08 to 24 hours, more preferably, 0.1 to 15 hours, even more preferably, 1 to 10 hours, yet more preferably, 2 to 7 hours and most preferably, 4 to 6 hours.

Preferably, the triptane selectivity is at least 7%, more preferably, at least 9%. For example, the triptane selectivity may be between 9 and 60% of the initial hydrocarbon feedstock.

The isomerisation catalyst employed is preferably a superacid. Suitable superacids include those comprising a Lewis acid of the formula $MX_n$, where M is an element selected from the transition metal series, Group 13, 14, 15 or 16 of the Periodic Table, X is a halogen, or an anion derived from fluorosulfuric acid, trifluoromethanesulfonic acid, or trifluoroacetic acid. n is an integer of 3 to 6. Bronsted acids selected from HX, where X has the same meaning as discussed above and mixtures thereof may also be employed.

Preferably, M is selected from Groups 13 and 15 of the Periodic Table. More preferably, M is Sb. X may be F, Cl, Br or I, and is preferably F or Cl. In preferred embodiments of the invention, M is employed in its highest valency state with the selected halogen. For example, in a most preferred embodiment of the invention, the Lewis acid is $SbF_5$.

M may alternatively be selected from the transition metal series. Where M is a transition metal, it is preferably a metal from Group IV or V of the transition metal series. Preferred transition metals include Ti, Zr, Hf, V, Nb, Ta. More preferably, M is selected from Ti, Nb and Ta, and most preferably, M is Ta.

Preferably, the Bronsted acid is selected from HF, trifluoromethanesulfonic and fluorosulfuric acid.

Preferred examples of suitable isomerisation catalysts are $HSO_3F$—$SbF_5$ and $SbF_5$—HF.

The molar ratio of Bronsted acid to Lewis acid can range from about 20:1 to 1:5. Preferably, a 5:1 to 1:1 molar ratio is employed. The amount of the catalyst employed with reference to the total amount of hydrocarbon used may range from about 0.01 to 100 parts by weight of the catalyst per part by weight of hydrocarbon. Preferably, the amount of catalyst employed is 1 to 10 parts by weight of the catalyst per part by weight of the hydrocarbon.

The catalyst may be used as the neat liquid, as a diluted solution or adsorbed on a solid support. With regard to the diluted catalyst, any diluent may be used that is inert under the reaction conditions. To obtain optimum results, the diluents may be pretreated to remove catalyst poisons such as water, unsaturated compounds and the like. Typical diluents include sulfuryl chloride fluoride, sulfuryl fluoride, fluorinated hydrocarbons and mixtures thereof. Protic acids including fluorosulfuric acid, surfuric acid, trifluoromethanesulfonic acid and the like, themselves, can be used as diluents. The diluent:catalyst volume ratio can range from about 50:1 to 1:1 and, preferably, from 10:1 to 2:1.

The catalyst may alternatively be incorporated with a suitable solid carrier or support. Any solid catalyst support may be used that is substantially inert to the catalyst under the reaction conditions. The support may be pretreated, such as by heating, chemical treatment or coating, to remove substantially all water and/or hydroxylic sites that might be present. Active supports may be rendered inert by coating them with an inert material such as antimony trifluoride or aluminium trifluoride. Suitable solid supports include carbon (eg graphite), fluoride-treated or coated resins such as sulfonated cation exchange resins, fluoride-treated acidic chalcides such as alumina and aluminosilicates, and acid-resistant molecular sieves such as a zeolite, e.g. faujasite. The supported catalysts can be prepared in any suitable manner, such as by conventional methods including dry mixing, coprecipitation or impregnation. In one embodiment, the supported catalyst is prepared by impregnating a suitable deactivated support with a metal fluoride such as antimony pentafluoride and then with a Bronsted acid such as fluorosulfuric acid.

When a supported catalyst is employed, the weight ratio of the Lewis acid to the support may range from 1:100 to 1:10 and preferably, from 1:50 to 1:35. The weight ratio of the Bronsted acid to the support may range from 1:100 to 1:10 and, preferably, from 1:50 to 1:35.

The hydrocarbon feedstock that may be used in the instant process include paraffins, alkyl substituted aromatic hydrocarbons and mixtures thereof. The paraffins as herein defined include aliphatic and cycloaliphatic hydrocarbons that are substantially in the liquid phase at room temperature. The aliphatic hydrocarbons (straight and branched chain materials) can contain 4 to 20 carbon atoms per molecule, preferably 4 to 8 carbon atoms, and may be exemplified by n-butane, n-pentane, methylpentane, methylhexane and the like. The cycloaliphatic hydrocarbons (naphthenes) can contain 6 to 20 carbon atoms per molecule, preferably 6–12 carbon atoms, and may be exemplified by methylcyclopentane, the dimethylcyclopentanes, ethyleyclohexane, n-pentylcyclohexane and the like. Depending on reaction conditions, summarization of the ring, i.e. ring expansion or contraction, may compete with side chain isomerisation. The alkyl substituted aromatic hydrocarbons can contain 7 to 20 carbon atoms per molecule, preferably 7 to 12 carbon atoms, and may include in principle all isomerisable alkylaromatic or polyalkylaromatic hydrocarbons such as the xylenes, n-butyl benzene and the like. Both positional isomerisation of the alkyl groups substituted on the ring and side chain isomerisation may occur depending on reaction conditions. Other aliphatic or alicyclic hydrocarbons commonly found in conventional petroleum hydrocarbon light naphtha streams may also be present.

In a preferred embodiment of the invention, the hydrocarbon feedstock comprises a $C_5$ to $C_9$ alkane, for example, a $C_7$ alkane. $C_7$ naphtha streams, for instance, may be employed. Examples of suitable $C_7$ alkanes include n-heptane, 2-methyl hexane, 3-methyl hexane, ethyl pentane, 2,3-dimethyl pentane, 3,3-dimethyl pentane. 2,2-diemethyl pentane and 2,4-dimethyl pentane. The hydrocarbon feedstock may consist essentially of one of these $C_7$ alkanes, or may comprise a mixture of two or more of them. Suitable alkane mixtures include mixtures of 3-methyl hexane and 2,3-dimethyl pentane and mixtures of heptane and 2,4-dimethyl pentane. The $C_7$ alkanes may be present in combination with other hydrocarbon species such as naphthenes (eg 0 to 40%, preferably 30 to 36%), and aromatics, such as toluene (eg 0 to 10%, preferably 2 to 5%). An example of such a combination comprises 25 to 40%, preferably, 32 to 38% n-heptane; 10 to 28%, preferably, 15 to 23% mono-branched heptane; 5 to 15%, preferably, 7 to 11% dibranched heptane; 20 to 40%, preferably, 32 to 38% naphthenes and 0 to 5%, for example, 2 to 3% aromatics. Preferably, however, the aromatic content of the feeds is low, for example, less than 1%. The $C_7$ alkanes may also be present in the feed together with other alkanes such as $C_5$, $C_6$ and $C_8$ alkanes. An example of such a mixture is an alkylate-$C_7$ stream comprising 2 to 6, preferably, 4% i-$C_5$; 3 to 7, preferably, 5% $C_6$; 50 to 70, preferably, 60 to 62% 2,3-dimethyl pentane; 20 to 30, preferably, 22 to 26% 2,4-dimethyl pentane and 2 to 8, preferably, 4 to 6% $C_8$.

The hydrocarbon feedstock may contain various cracking inhibitors or moderators such as hydrogen and/or iso-butane. The inhibitors act to depress excessive cleavage reactions that may occur during the isomerisation. When hydrogen or iso-butane is used, it is employed in amounts ranging, preferably, from 1 to 3 mole percent based on hydrocarbon feed.

The process of the invention may be conducted as a batch or continuous type operation. In general, the various means customarily employed in extraction processes to increase the contact area between the hydrocarbon phase and the catalyst phase may be used. In one embodiment of the invention, the hydrocarbon phase and catalyst phase may be contacted substantially in the liquid phase. The apparatus employed may be of a conventional nature. For example, the apparatus may comprise a single reactor, such as a fluidised-bed reactor, or multiple reactors provided, for example, with efficient stirring devices, such as mechanical agitators, ultrasonic agitators, jets of restricted internal diameter, and turbo mixers. The hydrocarbon phase and the catalyst phase may be passed through one or more reactors in concurrent, cross-current or counter-current flow. Unreacted reactants, catalysts, inhibitors and heavier products of the reaction may be separated from the desired isomeric product and from one another such as by distillation and returned in whole or in part to the isomerisation reaction. The resultant product may be further processed as by alkylation and the like, or be employed directly as a high octane gasoline blending agent.

The triptane product may be recovered from the product mixture using any suitable technique. Examples include distillation, extractive distillation, and selective crystallisation. Membranes may also be employed.

According to a further aspect of the present invention, there is provided a continuous process for the production of triptane, said process comprising:

feeding a hydrocarbon feedstock into a reactor, contacting the feedstock with an isomerisation catalyst, under reaction conditions effective to produce a product mixture comprising triptane, characterised in that the product mixture comprises at least two liquid phases, one liquid phase being denser than the other.

The two liquid phases may be separated by simple separation techniques, such as decantation. This separation step may be carried out continuously or at periodic intervals.

The denser of the two liquid phases is typically a polar or ionic phase comprising the isomerisation catalyst, and optionally, any catalyst diluent and/or catalyst support employed in the reaction. The denser liquid phase may be retained in the reactor. Alternatively, the denser liquid phase may be recovered from the reactor, and recycled, preferably, once at least some of the catalyst diluent has been removed from the recovered phase. The catalyst may also be regenerated prior to recycling. It should be noted that the denser of the two phases may be present as an emulsion.

The less dense of the two liquid phases is typically a less or non-polar phase comprising the triptane product. Optionally, other oily products, such as by-products of the reaction may also be present in the second phase. Examples of possible by-products include aliphatic hydrocarbons, for example, those comprising 3 to 10 carbon atoms. Other by-products include aromatic and polymeric species ($C_{12}$ and above). Such species may be fluorinated and/or sulphonated. In a preferred embodiment, the less dense phase is separated from the denser phase, and recovered from the reactor.

In addition to the two liquid phases, the product mixture may also comprise a vapour phase. The vapour phase may comprise triptane, other light aliphatic and aromatic hydrocarbons (eg $C_1$ to $C_9$), hydrogen and iso-butane. In a preferred embodiment, at least some of the vapour phase is withdrawn from the reactor. The vapour phase may be purified by condensation and distillation to produce a triptane-containing stream.

Any triptane recovered from the vapour phase may be used in the production of motor or aviation gasoline, especially, unleaded motor or unleaded aviation gasoline. In a preferred embodiment, the condensed vapour is purified further, for example, by distillation, to enhance its concentration of triptane. The remainder of the condensed vapour may be recycled to the reactor. At least one motor or aviation gasoline additive may then be added to the triptane-enhanced product. The resulting mixture may be employed as, or as an additive for a motor or aviation gasoline, preferably, an unleaded motor or aviation gasoline.

The contents of the reactor may be mixed. This mixing step may be carried out using any suitable technique, for example, by using a mechanical stirrer, an ultrasonic agitator and/or by introducing a gas or liquid into the reactor. Any suitable mechanical stirrer may be employed. Gases that may be bubbled through the reactor to agitate its contents include nitrogen, argon, hydrogen and light hydrocarbons (eg methane, isobutane). Additionally or alternatively, the mixing may be achieved simply as a result of the reactants and/or catalyst being introduced into the reactor.

Although mixing is important for facilitating reaction, it can also inhibit the separation of the two liquid phases. This problem may be alleviated by reducing the rate of agitation. Preferably, however, at least a portion of the product mixture is at least partially shielded from the full force of the agitation, so that it can separate into at least two liquid phases.

Thus, according to a preferred embodiment, there is provided a continuous process for the production of triptane said process comprising:

providing a reactor having a reaction zone and a separation zone, feeding a hydrocarbon feedstock into a reactor, contacting the feedstock with an isomerisation catalyst, under reaction conditions effective to produce a product mixture comprising triptane, said process being characterised by having at least a portion of the product mixture in the separation zone, so that it can separate into at least two liquid phases.

The reaction zone and separation zone are preferably in fluid communication with each other. The reaction zone and separation zone may be provided in a single piece of apparatus, for example, by using a reactor having a reaction zone and a separation zone. An advantage of this arrangement is that it keeps pipe-work requirements to a minimum, reducing the material cost of the overall reactor. It should be noted, however, that it is possible to provide the reaction zone and separation zone using separate pieces of apparatus, for example, by coupling a reactor to a separation tank. Multiple reaction zones and/or separation zones may be employed. For example, a reactor having a reaction zone and a separation zone may be coupled to a separate separation tank.

In preferred embodiments of the invention, a reactor having at least one reaction zone and at least one separation zone is employed. For example, the reaction and separation zones may be separated using one or more grids and/or perforated plates. In use, the product mixture is allowed to flow freely between the reaction and separation zones through the apertures or perforations in the grid/plate. When the contents of the reactor on one side of the plate/grid is mixed, the reactor contents on the opposite side of the plate/grid is shielded at least in part from the fall force of the mixing. Thus, the reactor contents on the opposite side of the grid is in the separation zone, and can separate into at least two phases. The stirrer may be employed in combination with one or more baffles, which may be located in the reactor to enhance the mixing effect of in the reaction zone.

The grid or perforated plate may be located in the reactor and placed 0 to 60°, preferably, 0 to 45°, more preferably, 0 to 30° and most preferably, 0 to 15° to the horizontal. In one embodiment, the grid or plate is positioned substantially horizontally. The reactor contents below the grid or plate is agitated, allowing the separation zone to form above the grid or plate. Preferably, the edge(s) of the grid or plate is adjacent to the inner walls of the reactor. The edge(s) may be spaced or in physical engagement with the inner walls of the reactor.

In the embodiment described above, the contents of the reactor is allowed to flow relatively freely through the apertures or perforations of the grid/plate. In an alternative embodiment, the flow of product mixture from the reaction zone to the separation zone may be driven by a mechanical impellor or by the gas lift effect of any bubbles in the reactor. Flow through the separation zone in this mode may be controlled, for example, by positioning a barrier or weir between the reaction zone and separation zone and controlling the driving force across it by controlling the liquid/vapour or liquid/liquid interface levels on either side. Thus, product mixture is allowed to flow from the reaction zone to the separation zone either continuously or at periodic intervals.

The hydrocarbon feedstock may be introduced continuously or at periodic intervals. Preferably, the feedstock is fed to the reactor continuously. The feedstock may be fed into the reactor at a rate of more than 25 g of hydrocarbon per kg of catalyst per hour, for example, from 50 to 2500 g of hydrocarbon per kg of catalyst per hour.

BRIEF DESCRIPTION OF THE DRAWINGS

These and other aspects of the present invention will now be described with reference to the drawings, in which.

DETAILED DESCRIPTION OF PREFERRED EMBODIMENTS

Figure 1:
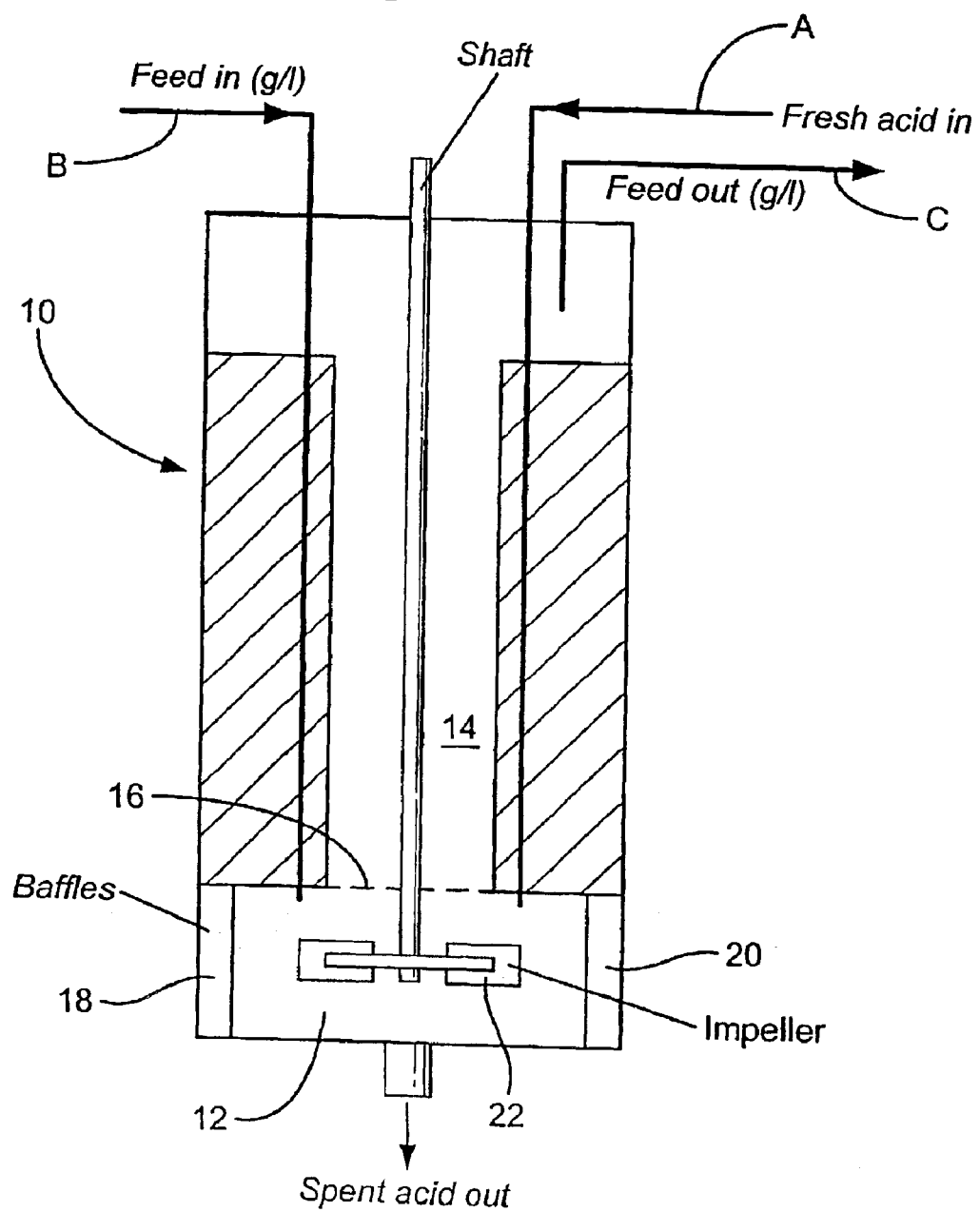
FIG. 1 is a schematic diagram of an apparatus suitable for carrying out an embodiment of the process of the invention.

Referring to FIG. 1, the apparatus comprises a reactor 10, which is divided into a reaction zone 12 and a separation zone 14 by a grid 16. The reactor is provided with a pair of baffle plates 18, 20 and a mechanical stirrer 22. The stirrer 22 extends into the reaction zone 12.

In operation, the reaction zone 12 is charged with 30 mol % $SbF_5$ in $FSO_3H$ via line "A". A reactant stream comprising naphtha is also continuously fed to the reaction zone 12 via line "B", and the contents of the reaction zone 12 is agitated by the mechanical stirrer 22. The reaction zone 12 is maintained at −30 to 10° C., and a pressure of less than 50 bar. Under the reaction conditions, the naphtha is isomerised to produce a product mixture comprising triptane.

The contents of the reactor 10 is free to flow between the reaction zone 12 and the separation zone 14 through the apertures (not shown) of the grid 16. The grid 16, however, shields the product mixture in the separation zone at least in part from the full force of the agitation caused by the stirrer 22. Thus, the product mixture in the separation zone 14 is allowed to settle and separate into a less dense phase, and a dense phase. The less dense phase contains the triptane product, and is continuously recovered from the separation zone via line "C". The dense phase may be present as an emulsion because of the agitational forces in the reaction zone 12.

Figure 2:
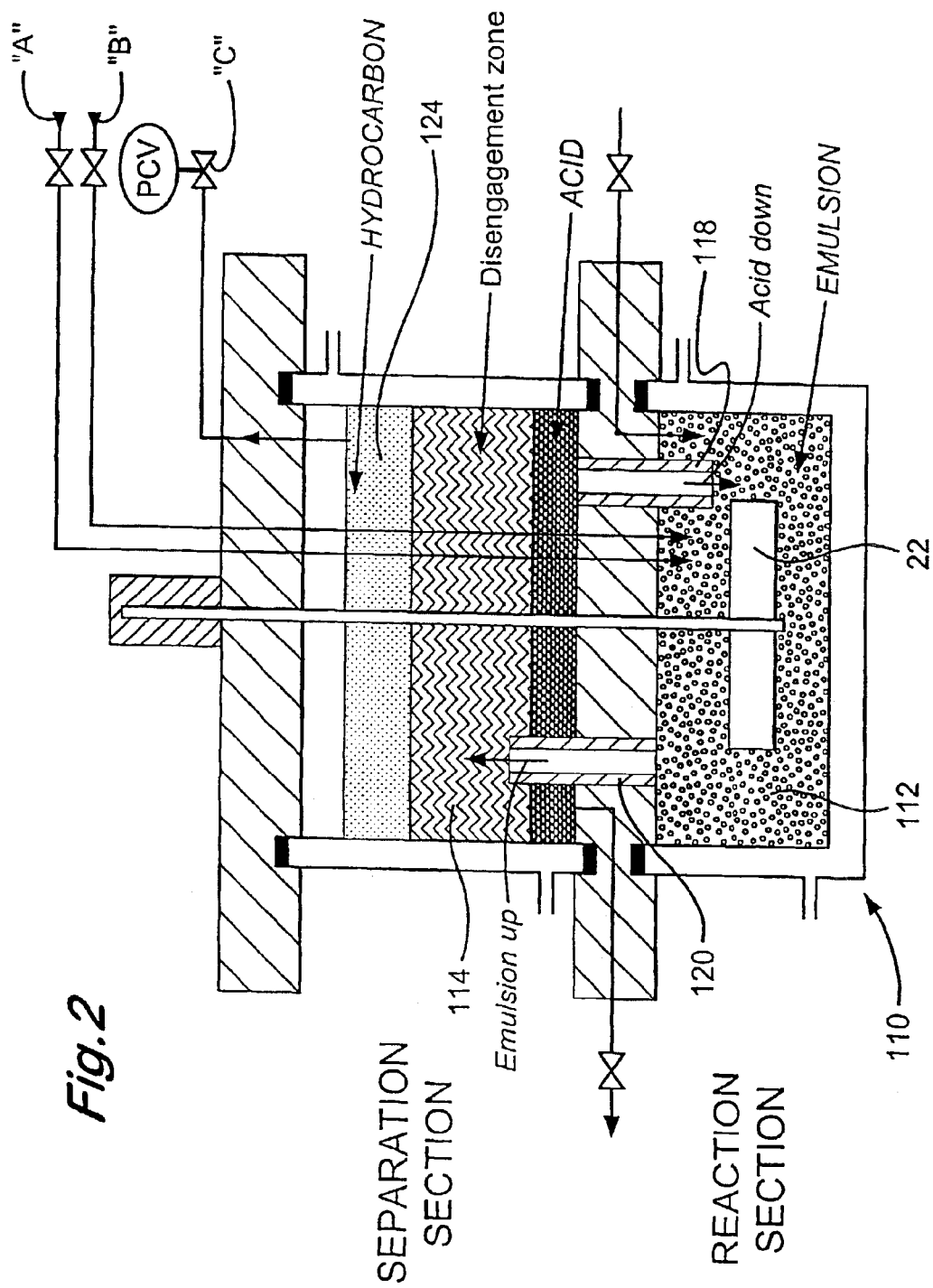
FIG. 2 is a schematic diagram of an alternative apparatus suitable for carrying out an embodiment of the process of the invention.

FIG. 2 depicts an alternative apparatus for carrying out an embodiment of the present invention. The apparatus comprises a reactor 110, which is divided into a reaction zone 112 and a separation zone 114 by a separator 116. The separator 116 comprises an inlet 118, and an outlet 120. The reactor 110 is also provided with a mechanical stirrer 122, which extends into the reaction zone 112.

In operation, the reaction zone 112 is charged with 30 mol % $SbF_5$ in $FSO_3H$ via line "A". A reactant stream comprising naphtha is also continuously fed to the reaction zone 112 via line "B", and the contents of the reaction zone 112 is agitated by the mechanical stirrer 122. The reaction zone 112 is maintained at −30 to 10° C., and a pressure of less than 50 bar. Under the reaction conditions, the naphtha is isomerised to produce a product mixture comprising triptane.

The reaction mixture of the reaction zone 112 is present as an emulsion because of the agitational forces caused by the stirrer 122. The reaction mixture of the reaction zone 112, however, is free to flow from the reaction zone 112 into the separation zone 114 via the outlet 120 of the separator 116. In the separation zone, the reaction mixture is shielded from the full force of the agitation caused by the stirrer 122. Thus, the reaction mixture is allowed to settle and separate into three phases: a less dense phase 124, a middle phase 126 and a dense phase 128. The less dense phase 124 contains the triptane product, and is continuously recovered from the separation zone via line "C". The dense phase 128 comprises the acid catalyst (30 mol % $SbF_5$ in $FSO_3H$). Some of this phase 128 is allowed to flow back into the reaction zone 112 via the inlet 118.

EXAMPLES

A hydrocarbon (100 ml) was intimately mixed with a dense catalyst consisting of 30 mol % $SbF_5$ in $FSO_3H$ in a batch autoclave at temperature of −30 to 10° C. To ensure good mixing a baffle was employed, and the reaction mixture was stirred at 2000 rpm. Samples were removed from the reaction mixture at timed intervals and analysed by gas chromatography. The results are shown in Table 1 below.

| Feed | Temp ° C. | Res. time minutes | Selectivity 223TMB % | Selectivity $C_7$ Isom % | Conv. % | Yield 223TMB wt % |
|---|---|---|---|---|---|---|
| Heptane | −30 | 7440 | 12.8 | 94.4 | 68.3 | 8.7 |
| " | −20 | 1890 | 11.4 | 94.2 | 45.3 | 5.2 |
| " | −10 | 300 | 10.4 | 93.8 | 50.5 | 5.3 |
| " | 0 | 120 | 8.6 | 91.4 | 26.8 | 2.3 |
| " | 10 | 25 | 8.5 | 94.6 | 9.9 | 0.8 |
| 3MHx | −30 | 4260 | 15.9 | 99.8 | 87.0 | 13.8 |
| " | −20 | 525 | 15.1 | 92.7 | 85.1 | 12.9 |
| " | −10 | 90 | 10.0 | 96.1 | 82.1 | 8.2 |
| " | 0 | 36 | 8.0 | 97.7 | 80.0 | 6.4 |
| 23DMP | −30 | 4260 | 14.4 | 99.8 | 90.0 | 13.0 |
| " | −20 | 1440 | 13.9 | 91.4 | 92.2 | 12.8 |
| " | −10 | 310 | 13.4 | 93.6 | 92.1 | 12.3 |
| " | 0 | 75 | 11.7 | 91.6 | 91.9 | 10.8 |
| 3MHx/23DMP | −30 | 4860 | 16.2 | 99.7 | 78.0 | 12.6 |
| 3MHx/23DMP | −20 | 1020 | 15.1 | 99.7 | 77.0 | 11.6 |
| 3MHx/23DMP | −10 | 310 | 14.0 | 90.4 | 72.7 | 10.2 |
| 3MHx/23DMP | 0 | 60 | 10.0 | 99.6 | 76.0 | 7.6 |
| Heptane/24DMP | −30 | 4200 | 14.5 | 99.8 | 59.0 | 8.6 |
| Heptane/24DMP | −20 | 1044 | 13.8 | 99.6 | 58.0 | 8.0 |
| Heptane/24DMP | −10 | 240 | 12.2 | 99.6 | 54.0 | 6.6 |
| Heptane/24DMP | 0 | 60 | 10.6 | 99.5 | 51.0 | 5.4 |
| 24DMP | −30 | 3600 | 15.6 | 99.8 | 75.0 | 11.7 |
| " | −20 | 900 | 15.0 | 99.7 | 75.0 | 11.3 |
| " | −10 | 240 | 14.2 | 99.6 | 74.0 | 10.5 |
| " | 0 | 60 | 12.5 | 99.6 | 74.0 | 9.3 |

Key: heptane = n-heptane; 3MHx = 3-methyl hexane; 23DMP = 2,3-dimethyl pentane; 24DMP = 2,4-dimethyl pentane; conv. = conversion; res. = residence As can be seen from the data, the selectivity of the process towards triptane is at least 8.0% under the reaction conditions are employed.

What is claimed is:

1. A process for the production of triptane, said process comprising:
    isomerising a naphtha stream comprising a major amount of $C_5$ to $C_8$ hydrocarbons and being a $C_7$ naphtha stream comprising at least one of n-heptane, 2-methyl hexane, 3-methyl hexane, ethyl pentane, 2,3-dimethyl pentane, 3,3-dimethyl pentane, 2,2-dimethyl pentane and 2,4-dimethyl pentane by contacting said feedstock with an isomerisation catalyst which is a superacid comprising $HSO_3F$—$SbF_5$ at a reaction temperature of −50 to 25° C., and a contact time of 0.01 to 150 hours, such that the triptane selectivity of the isomerisation reaction is at least 5 wt % as a proportion of said hydrocarbon feedstock.

2. A process as claimed in claim 1, wherein the reaction temperature is −30 to 15° C.

3. A process as claimed in claim 1, wherein the contact time is 0.08 to 24 hours.

4. A process as claimed in claim 1, wherein the triptane selectivity is between 9 and 60 wt % of the initial hydrocarbon feedstock.

5. A process as claimed in claim 1, wherein the catalyst is employed as a solution.

6. A process as claimed in claim 5, wherein the catalyst is dissolved in a diluent selected from the group consisting of sulfuryl chloride fluoride, sulfuryl fluoride, fluorinated hydrocarbons, fluorosulfuric acid, sulfuric acid, trifluoromethanesulfonic acid and mixtures thereof.

7. A process as claimed in claim 1, wherein the catalyst is adsorbed on a solid support.

8. A process as claimed in claim 1, which is carried out in a batch manner or continuously.

9. A process as claimed in claim 8 wherein the process is a continuous process for the production of triptane, said process further comprising:
    feeding a hydrocarbon feedstock into a reactor,
    contacting the feedstock with an isomerisation catalyst, under reaction conditions effective to produce a product mixture comprising triptane,
    characterised in that the product mixture comprises at least two liquid phases, one liquid phase being denser than the other.

10. A continuous process as claimed in claim 9, wherein one of the two liquid phases is separated from the other by decantation.

11. A continuous process as claimed in claim 9, wherein the denser of the two liquid phases is either
    retained in the reactor, or
    recovered from the reactor, purified and recycled.

12. A continuous process as claimed in claim 10, wherein the less dense of the two liquid phases is separated from the denser phase, recovered from the reactor, and optionally, purified to increase its concentration of triptane.

13. A continuous process as claimed in claim 9, wherein in addition to the two liquid phases, the product mixture also comprises a vapour phase.

14. A continuous process as claimed in claim 13, wherein the vapour phase is condensed and optionally purified to produce a triptane-containing stream.

15. A continuous process as claimed in claim 9, which comprises:
   providing a reactor having a reaction zone and a separation zone,
   feeding a hydrocarbon feedstock into a reactor,
   contacting the feedstock with an isomerisation catalyst, under reaction conditions effective to produce a product mixture comprising triptane,
   said process being characterised by having at least a portion of the product mixture in the separation zone, so that it can separate into at least two liquid phases.

16. A continuous process as claimed in claim 15, wherein the reaction zone and separation zone are in fluid communication with each other.

17. A continuous process as claimed in claim 16, wherein the reaction zone and separation zone are separated using one or more grids and/or perforated plates.

18. A continuous process as claimed in claim 17, wherein the reactor contents on one side of the grid or plate is agitated, allowing the separation zone to form on the opposite side of the grid or plate.

19. A process as claimed in claim 1, wherein the feedstock contains cracking inhibitors or moderators selected from the group consisting of hydrogen and isobutene.

* * * * *

UNITED STATES PATENT AND TRADEMARK OFFICE
CERTIFICATE OF CORRECTION

PATENT NO. : 6,855,857 B2
DATED : February 15, 2005
INVENTOR(S) : Boesveld et al.

It is certified that error appears in the above-identified patent and that said Letters Patent is hereby corrected as shown below:

Column 10,
Line 16, please change "isobutene" to -- isobutane --.

Signed and Sealed this

Thirty-first Day of May, 2005

JON W. DUDAS
*Director of the United States Patent and Trademark Office*